United States Patent [19]

Watson

[11] Patent Number: 4,840,794

[45] Date of Patent: Jun. 20, 1989

[54] MASTITIS VACCINE CONTAINING ANTIGENS FROM S. AUREUS

[75] Inventor: Dennis L. Watson, Armidale, Australia

[73] Assignee: Commonwealth Scientific and Industrial Research Organization, Australia

[21] Appl. No.: 12,060

[22] PCT Filed: May 13, 1986

[86] PCT No.: PCT/AU86/00134

§ 371 Date: Jan. 12, 1987

§ 102(e) Date: Jan. 12, 1987

[87] PCT Pub. No.: WO86/06634

PCT Pub. Date: Nov. 20, 1986

[30] Foreign Application Priority Data

May 13, 1985 [AU] Australia .................. 528/85

[51] Int. Cl.$^4$ .......................... A61K 37/085
[52] U.S. Cl. .................. 424/92; 435/252.1; 435/883; 435/253.6; 424/85.8
[58] Field of Search .............. 424/92, 85, 85.8; 435/252.1, 253.6, 883

[56] References Cited

U.S. PATENT DOCUMENTS

| | | | |
|---|---|---|---|
| 4,327,082 | 4/1982 | Armitage | 424/92 |
| 4,425,330 | 1/1984 | Norcross et al. | 424/92 |
| 4,591,499 | 5/1986 | Linn et al. | 424/92 X |

FOREIGN PATENT DOCUMENTS

| | | |
|---|---|---|
| 2149/61 | 3/1961 | Australia . |
| 17681/62 | 5/1962 | Australia . |
| 35580/63 | 9/1963 | Australia . |
| 85929/82 | 7/1981 | Australia . |
| 1182555 | 8/1968 | United Kingdom . |

OTHER PUBLICATIONS

Infection & Immunity, Jul. 84, pp. 87–93, vol. 45, No. 1, Fournier et al., "Purification . . . *Staphylococcus aureus* Type 8. . . ".

Carb. Research, 117 (1983), 113–123, Murphy et al., "Repeating Sequence of . . . Capsular Polysaccharide".

Chem. Ab., vol. 100, 1984, p. 292 (100:20338c) "Models to Study Antigenic and Virulence Prop . . . ".

Chem. Ab., vol. 96, 1982, p. 384 (96:177569a) "Capsular Polysaccharides of *Staphylococcus aureus*".

Chem. Abstracts, 91 (1979), 173120w, Watson et al.

*Primary Examiner*—Howard E. Schain
*Attorney, Agent, or Firm*—Bacon & Thomas

[57] ABSTRACT

A killed vaccine effective in the immunization of ruminants against intramammary challenge by *S. aureus*, comprises antiphagocytic in vivo antigen(s) produced by a pseudocapsule-producing strain of *S. aureus*. An in vitro method of cultivating *S. aureus* under "simulated in vivo conditions" is also disclosed, together with methods for the production and use of the killed vaccine.

14 Claims, No Drawings

MASTITIS VACCINE CONTAINING ANTIGENS FROM S. AUREUS

This invention concerns the immunisation of ruminants, including cattle, sheep and goats, against staphylococcal mastitis.

Staphylococcal mastitis is a condition affecting approximately 25% of Australian dairy cattle, which is estimated to cost the industry about $50,000,000 each year in lost milk production, culling, antibiotics and costly husbandry procedures.

Traditionally the disease is treated, on the appearance of clinical signs, by the infusion of antibiotics which are active against the infective organism Staphylococcus aureus. Such an approach is far from ideal. Apart from being curative rather than preventative, there are economic considerations such as the need for identification and individual treatment of affected animals and the unsuitability of antibiotic-contaminated milk for human consumption or processing. An additional problem is the increasing development of antibiotic-resistant strains of S.aureus. Attention has, therefore, turned towards the possibility of immunising animals against the infection.

Numerous attempts have been made to systemically immunise ruminants against mastitis pathogens using conventionally prepared vaccines delivered either subcutaneously or intramuscularly. Killed bacterial cells (Derbyshire (1960b), isolated bacterial cell walls (Singleton et al 1967), toxoids (Minett 1939), killed cell-toxoid preparations (Bracewell and Pattison 1958) all have been tried with and without immunological adjuvants (Derbyshire 1961a). In some of these experiments a degree of protection has been achieved but overall the results have been disappointing. In view of the outstanding successes of other systemically delivered bacterial vaccines in ruminants (for example, Clostridial vaccines, Brucella abortus strain 19) the failure of mastitis vaccines generally has been attributed to the efficiency of the blood-milk barrier in preventing all but small quantities of circulating antibody from reaching the milk (Lascelles and McDowell 1974).

There have been reports in the literature which (despite experimental limitations in each case) . are extremely interesting because of the apparent success achieved when immunising sheep (Bridre 1907) and goats (Derbyshire 1961b) with live S.aureus vaccines (given subcutaneously). In both of these studies it was reported that the vaccinated animals were highly resistant to subsequent intramammary challenge with virulent S.aureus. More recently research has confirmed the protective capability of a live S.aureus vaccine in ewes (Watson and Lee 1978) and elucidated some of the mechanisms which are probably involved. Live S.aureus vaccines stimulate the synthesis of considerable quantities of $IgG_2$ antibody which is cytophilic for neutrophils and there is direct evidence that this antibody enhances the specific phagocytic capacity of neutrophils for S.aureus under in vitro conditions (Watson 1975b, 1976). In contrast to live staphylococcal vaccines which stimulate predominantly $IgG_2$ synthesis (Kennedy et al 1981, Kennedy and Watson 1982), killed staphylococcal vaccines given with oily adjuvants stimulate the production of predominantly $IgG_1$ antibody (Yokomizo and Isayama 1978; Kennedy and Watson 1982). Thus at least one probable reason for the relatively poor results with killed S.aureus vaccines in prophylaxis of staphylococcal mastitis is that they do not stimulate synthesis of sufficient quantities of the subclass of IgG which mediates protection through its opsonising activity Furthermore, recent studies in non-lactating ewes have shown that a live S.aureus vaccine was superior to a killed vaccine in promoting an enhanced neutrophil response in the mammary gland to a subsequent intramammary challenge with viable staphylococci of a heterologous strain (Colditz and Watson 1982a, 1982b). The live vaccine, therefore, results in more neutrophils arriving in the secretion within a few hours of infection and these cells are "armed" with cytophilic $IgG_2$ which increases their phagocytic capacity for staphylococci. In remains to be determined whether live staphylococcal vaccines can protect against the diversity of strains of S.aureus which may cause mastitis although recent experiments have provided encouraging results following challenge with homologous or heterologous strains in both ewes and heifers (Watson and Kennedy 1981; Watson 1984a). Australian Patent Specification No.85929/82 discloses a live vaccine effective in the immunisation of ruminants against intermammary challenge by homologous or heterologous strains of S.aureus which is prepared by attenuating a catalase- and coagulase-positive strain of S.aureus, of ruminant origin, by multiple passage until loss of haemolytic activity is observed It has been known for many years that the metabolic and antigenic characteristics of pathogenic microorganisms may be quite different when growing in vivo compared with growth in standard, in vitro laboratory conditions (Beining and Kennedy 1963). In vivo-grown S.aureus, isolated from clinical mastitis cases, are more virulent and usually have an anti-phagocytic pseudocapsule in contrast to the same strain of staphylococci grown in vitro (Watson and Prideaux 1979; Watson 1982; Norcross and Opdebeek 1983). These features provide an additional explanation for the success of live S.aureus vaccines. Organisms grown in the laboratory and killed for a vaccine would not contain immunogenic quantities of anti-phagocytic pseudocapsular antigens and therefore the antibody produced in response to such vaccines is not directed against these protective antigens. In contrast, the in vivo multiplication of staphylococci given as a live vaccine ensures the presentation of these "in vivo" pseudocapsular antigens and the production by the animal of antibody against these antigens.

The present invention concerns a killed vaccine capable of generating practical immunity against staphylococcal mastitis, and to methods for the production and use of such a vaccine.

In its broadest aspect, the present invention provides a killed vaccine effective in the immunisation of ruminants against intramammary challenge by S.aureus and other species of the genus Staphylococcus, which comprises the anti-phagocytic in vivo antigen(s) produced by a pseudocapsule-producing strain of S.aureus.

As discussed above, it has been found (Watson and Prideaux 1979; Watson 1982) that in vivo-grown S.aureus has an enhanced virulence which is likely to be due, at least partially, to the expression of anti-phagocytic in vivo antigen which is a characteristic of pseudocapsule-producing strains of S.aureus. S.aureus in general is not an encapsulated species of bacteria, however encapsulated strains are known which provide exceptions to this rule. The production of a capsule by such strains when grown under conventional laboratory conditions can be readily demonstrated by an established and widely used technique (the India ink technique—Butt 1936), which identifies the strains as encapsulated *S.aureus*. Strains of *S.aureus* which produce a pseudocapsule can be distinguished from such encapsulated strains in that the pseudocapsule-producing strains are negative in the India ink test when grown under conventional laboratory conditions (in vitro) or under in vivo conditions. However, when grown under in vivo conditions or when isolated from clinical material, they do produce a substance on the outside of the cell wall which is variously described as a "pseudocapsule" or "glycocalyx" (Caputy and Casterton, 1982). The studies referred to earlier have described additional antigen(s) in in vivo-grown *S.aureus* which is not present when the same strain is grown under in vitro conditions, this additional antigen being identified as the "in vivo antigen(s)" and forming part of the pseudocapsule. As described earlier, (Watson 1982), the "in vivo antigen(s)" is not the same substance as the extracellular slime produced by *S.aureus* under certain conditions, nor can it be visualised as a capsular structure. Although the precise nature of the "in vivo antigen(s)" has not yet been ascertained, it is generally accepted that the pseudocapsule is largely polysaccharide. It is believed, however, that at least one important component of the pseudocapsule is protein or glycoprotein in nature, based on absorption at a wavelength of 280 m$\mu$, staining of bands in polyacrylamide gels, and positive reaction with biuret reagent. It is an important feature of this aspect of the present invention that it provides a killed vaccine which comprises this in vivo antigen(s).

Whilst it has been discovered that in vivo antigen(s) is present in the pseudocapsular material of a number of pseudocapsule-strains of *S.aureus* (Watson 1982), in a particularly preferred embodiment of this invention the killed vaccine comprises in vivo antigen(s) derived from a particular strain isolated from an acute case of bovine mastitis and identified as strain JG80. Strain JG80 fulfils all the requirements of a ruminant mastitis strain of *S.aureus* according to Bergey's Manual of Determinative Bacteriology This strain is Gram-positive with grape-like clusters of spherical cells, and is characterised by rounded, smooth creamy-white colonies on blood agar. In addition, it is both catalase- and coagulase-positive, and is capable of producing acid from mannitol. Strain JG80 is a weak producer of alpha-hemolysin and a very strong producer of beta-hemolysin.

*Staphylococcus aureus,* strain JG80, has been deposited at the American Type Culture Collection, in Rockville, Md., U.S.A., under A.T.C.C. No. 53486, on Apr. 30, 1986.

In a particularly preferred embodiment of the present invention, the vaccine also incorporates an adjuvant, in particular an adjuvant which promotes the production of IgG$_2$ subtype antibodies. It has been found that dextran sulphate is a particularly effective adjuvant for use in the vaccine of the present invention and it significantly enhances the protective immune response. This is believed to derive from the fact that dextran sulphate is a potent stimulator of IgG$_2$ antibody against staphylococcal cell surface antigens; as previously described, the presence of IgG$_2$ on the neutrophil membrane results in enhanced phagocytosis of *S.aureus* organisms in the mammary gland where neutrophils are the major defence mechanism against bacterial infection.

It has been noted above that strains of *S.aureus* which produce a pseudocapsule, when grown in the laboratory and killed for a vaccine, would not contain the antigenic material of the present invention. An important further feature of the present invention resides in the discovery of a method of production of this antigenic material which arises from a novel method of cultivating the pseudocapsule-producing strains of *S.aureus* which, in effect, enables cultivation under "simulated in vivo conditions".

According to this aspect of the present invention, there is provided a method of cultivation of a pseudocapsule-producing strain of *S.aureus* which is characterised in that organisms of the said strain of *S.aureus* are grown in vitro in a nutrient growth medium which has been enhanced by the addition of milk or milk components thereto.

In this particular aspect of the present invention, a preferred addition to the nutrient growth medium to enhance the medium is sterile milk whey, for example rennet whey. The precise nature of the milk or milk component such as milk whey which is effective in enhancing the medium to enable the "simulated in vivo conditions" is not known. Preliminary investigations in this regard appear to indicate that the lactose in the enhancing additive is not the crucial factor in ovine milk whey for induction of the in vivo antigen(s) in in vitro culture. These investigations have established that while the use of lactose alone as an additive does induce the synthesis of a pseudocapsule in in vitro culture, (although it is not as effective as milk whey in this regard), lactose does not appear to induce the synthesis of the in vivo antigen(s) at all.

In this aspect of the present invention, therefore it has been found that the enhancement of the nutrient growth medium by the addition of, for example, milk whey enables the in vitro culture of *S.aureus* in such a manner that the "in vivo antigen(s)" normally associated only with in vivo culture of these organisms are produced under in vitro conditions. Preferably, in order to reduce or avoid the risk of auto-immune reaction, it is advisable to use milk whey from a "foreign" ruminant species, that is in the production of a vaccine for use in cattle, it is advisable to use ovine or other non-bovine milk whey.

In a further aspect of the present invention, there is provided a method of producing a vaccine effective in the immunisation of ruminants against intramammary challenge by *S.aureus* and other species of the genus Staphylococcus, which comprises the steps of:

(i) growing a pseudocapsule- producing strain of *S.aureus* in vitro in a nutrient growth medium enhanced by the addition of milk or a milk component, and (ii) subsequently inactivating the bacteria.

The cultivation of the pseudocapsule-producing strain under "simulated in vivo conditions" results in the production of in vivo antigen(s) as part of the pseudocapsule as described above. Inactivation of the bacteria may be effected by any known means, for example, by addition of a bacteriocide such as formalin followed by storage between 2° C. and 8° C. for at least 24 hours. Preferably, after inactivation of the bacteria, the cells are separated from the supernatant, for example by centrifugation, and the cells are then suspended in a suitable sterile buffered medium. The final vaccine may also contain other known vaccine components such as bacteriostats In yet another aspect, there is provided a method of immunising a ruminant against staphylococcal mastitis, which comprises administering to the ruminant an effective amount of the vaccine in accordance with this invention.

While the essential component of the vaccine of the present invention is the in vivo antigen(s) component previously described, it is preferred that either the vaccine also include a toxoid component based on exo-toxins such as alpha- and beta-hemolysins secreted by S.aureus into a culture supernatant, or that such a toxoid component be administered simultaneously with the vaccine of this invention. The principal toxin in such a toxoid component is the toxin beta-hemolysin, a toxin produced by most ruminant mastitis strains of S.aureus in in vitro culture. After culture of the bacteria, for example for at least 36 hours in a fortified nutrient broth, the toxins can be readily harvested by centrifugation to separate cells and supernatant, followed by concentration of the supernatant by lyophilization and toxoiding by known methods, for example, with formalin. S.aureus JG80 described earlier is a very strong producer of beta-hemolysin, and is a preferred strain for production of the toxoid component when cultured under conditions favouring secretion of exotoxins, typically by culture using a fortified nutrient broth.

It will be appreciated that in addition to the beta-hemolysin, S.aureus also secretes other extracellular products such as enzymes and other hemolysins (alpha-, gamma- and delta-hemolysins) and all such other extracellular products may be toxoided and incorporated into the toxoid component described above.

The inclusion of the toxoid component as described herein, either in the vaccine itself, or in the vaccination regimen, is of particular benefit in providing protection against highly toxigenic strains of S.aureus. Thus, while the vaccine of this invention based on in vivo antigen(s) provides good protection from challenge with low to moderately toxigenic strains, when the toroid component is included the protection against even highly toxigenic strains is substantial. Preferably, the toxoid component is combined with the in vivo antigen(s) component in a combined vaccine. Serological testing has shown that there is no significant difference in antibody titres to the in vivo antigen(s) or to beta-hemolysin when the components are administered simultaneously but in separate anatomical locations (for example, to avoid undesirable interactions between the lesions induced by each component) or together.

The vaccine of this invention may be formulated so as to include a "depot" component to increase retention of the antigenic material at the administration site. By way of example, in addition to the preferred adjuvant, dextran sulphate, mineral oil may be added to provide this depot effect.

The route of administration of the vaccine is not critical, and for example subcutaneous, intracutaneous and intramuscular injection may be used. The vaccine may also be administered intramammarily, if desired, in association with antibiotics. Finally, it will be appreciated by persons skilled in this field, that the vaccine of this invention may be combined with vaccines of other genera of bacteria to provide a single "broad spectrum" vaccine.

The invention will now be described by reference to specific Examples for the preparation of the vaccine of the invention, and of use thereof.

A. VACCINE PREPARATION

1. *Staphyloccocus aureus* (strain JG80) was grown from a starter culture for 24 hours in 1 liter of Oxoid nutrient broth to which had been added 10% (v/v) of sterile ovine milk whey. The culture was grown at 37° C. with shaking on an orbital shaker. After 24 h growth, formalin was added to a final concentration of 1% (v/v) and the culture was then held at 4° C. for 24 h. The cells were then removed by centrifugation at 7000 rpm (1 hour, 4° C.) and the supernatant discarded. The cells were resuspended in sterile phosphate buffered 0.9% saline pH 7.2 and adjusted to a concentration of $10^{10}$/ml spectrophotometrically. Thiomersal was added to a final concentration of 0.015% (w/v). Just prior to vaccination of the animals dextran sulphate (M.Wt=500,000) (Pharmacia Fine Chemicals) was added to this vaccine at a concentration of 50 mg/ml. The suspension was shaken vigorously for approximately 30 minutes. This is vaccine "C1".

2. *Staphyloccocus aureus* (strain JG80) was grown from a starter culture for 48 hours in 1 liter of Oxoid Brain-Heart Infusion broth. The culture was grown at 37° C. with very gentle shaking on an orbital shaker. The culture was centrifuged at 7000 rpm, 1 hour, 4° C. and 800 ml of the supernatant was concentrated by lyophilisation to a volume of 100 ml. To this was added 1 ml formalin and the preparation was allowed to stand at room temperature for at least 4 hours. This toxoid was then frozen ($-16°$ C.) in 10 ml aliquots and thawed immediately before use. This is vaccine "T1".

B: VACCINATION

Seven primaparous Australian Illawarra Shorthorn heifers were vaccinated at approximately 3 weeks partum. Seven similar heifers were unvaccinated controls.

Vaccine C1 was given as a 1 ml dose subcutaneously in the posterior aspect of the left hind limb approximately 50cm above the hock. Vaccine T1 was given as a 1 ml dose subcutaneously in the same location on the right hind limb.

Two weeks later the same vaccination regimen was repeated adjacent to the respective primary sites.

C: CHALLENGE

Three weeks after the secondary vaccination all the heifers were challenged by infusing approximately 1000 colony-forming units of S.aureus (strain Newbould 305) into the left fore gland.

Various measurements were made before and after challenge to assess the effect of vaccination on the response to challenge.

The data set out in Tables 1, 2 and 3 indicate that the vaccination protocol induced a substantial degree of protection from the challenge organisms.

The results of similar trials in ewes (challenged with S.aureus strain JG80 or Newbould 305), and cows (challenged with S.aureus strain 32V) are set out in Tables 4 and 5, and 6 and 7 respectively.

TABLE 1

Numbers of cows shedding S.aureus in milk following challenge with S.aureus strain N305. Data are numbers of cows shedding per number challenged.

| Time post-challenge (days) | Vaccinates | Controls |
| --- | --- | --- |
| 0 | 0/7 | 0/7 |
| one-half | 3/7 | 4/7 |
| 1 | 4/7 | 4/7 |
| 2 | 2/7 | 4/7 |
| 3 | 3/7 | 4/7 |
| 4 | 3/7 | 5/7 |

TABLE 1-continued

Numbers of cows shedding S.aureus in milk following challenge with S.aureus strain N305. Data are numbers of cows shedding per number challenged.

| Time post-challenge (days) | Vaccinates | Controls |
|---|---|---|
| 5 | 4/7 | 6/7 |
| 6 | 2/7 | 3/7 |
| 7 | 2/7 | 4/7 |
| 8 | 3/7 | 4/7 |
| 9 | 2/7 | 5/7 |
| 10 | 3/7 | 4/7 |
| 14 | 1/7 | 4/7 |
| 20 | 2/7 | 4/7 |
| 27 | 1/7 | 2/7 |

TABLE 2

Clinical mastitis cases in cows challenged with S.aureus strain N305. Data are numbers of cows clinical per number challenged.

| Time post-challenge (days) | Vaccinates | Controls |
|---|---|---|
| 0 | 0/7 | 0/7 |
| 1 | 0/7 | 1/7 |
| 2 | 1/7 | 1/7 |
| 3 | 1/7 | 2/7 |
| 4 | 1/7 | 2/7 |
| 5 | 1/7 | 2/7 |
| 6 | 1/7 | 2/7 |
| 7 | 1/7 | 2/7 |
| 8 | 1/7 | 2/7 |
| 9 | 1/7 | 2/7 |
| 10 | 1/7 | 3/7 |
| 14 | 1/7 | 1/7 |
| 21 | 0/7 | 1/7 |
| 27 | 0/7 | 1/7 |

TABLE 3

Milk production (expressed as a percentage of pre-challenge production) in cows following challenge with S.aureus strain N305. Values are means ± standard errors.

| Time post-challenge (days) | Vaccinates | Controls |
|---|---|---|
| 2 | 97 ± 2 | 89 ± 4 |
| 6 | 92 ± 4 | 78 ± 8 |
| 10 | 93 ± 4 | 84 ± 7 |
| 14 | 97 ± 2 | 88 ± 5 |
| 21 | 87 ± 6 | 73 ± 6 |
| 27 | 97 ± 1 | 82 ± 7 |

TABLE 4

Milk production (expressed as a percentage of pre-challenge production) in ewes vaccinated with the staphylococcal mastitis vaccine. Values are means ± standard errors.

| Time post-challenge (days) | Challenge strain of S.aureus | | | |
|---|---|---|---|---|
| | Strain JG80 | | Strain N305 | |
| | Vaccinates | Controls | Vaccinates | Controls |
| 3 | 54 ± 15 | 6 ± 4 | 100 ± 0 | 59 ± 17 |
| 8 | 62 ± 15 | 2 ± 1 | 86 ± 11 | 64 ± 20 |
| 15 | 57 ± 14 | 2 ± 1 | 89 ± 7 | 58 ± 16 |
| 25 | 52 ± 19 | 3 ± 2 | 87 ± 7 | 60 ± 16 |

TABLE 5

Clinical mastitis cases in ewes vaccinated with the staphylococcal mastitis vaccine. Data are numbers of ewes surviving the challenge.*

| Challenge strain of S. aureus. | Group | Time after challenge (days) | | | | | | | |
|---|---|---|---|---|---|---|---|---|---|
| | | 0 | 1 | 2 | 3 | 4 | 8 | 15 | 25 |
| Strain JG80 | Vaccinates | 0/5 | 1/5 | 1/5 | 1/4 | 2/4 | 2/4 | 1/4 | 1/4 |
| | Controls | 0/5 | 5/5 | 5/5 | 2/2 | 2/2 | 2/2 | 2/2 | 2/2 |
| Strain N305 | Vaccinates | 0/4 | 0/4 | 0/4 | 1/4 | 1/4 | 0/4 | 0/4 | 0/4 |
| | Controls | 0/5 | 4/5 | 4/5 | 2/5 | 3/5 | 2/5 | 1/5 | 2/5 |

*Animals which developed acute gangrenous mastitis were euthanased.

TABLE 6

Milk production (expressed as a percentage of pre-challenge production) in cows following challenge with S.aureus strain 32V. Values are means ± standard errors.

| Time post-challenge (days) | Vaccinates | Controls |
|---|---|---|
| 0 | 100 | 100 |
| 2 | 97 ± 2 | 70 ± 3 |
| 9 | 78 ± 10 | 65 ± 11 |
| 16 | 76 ± 10 | 65 ± 11 |
| 23 | 75 ± 10 | 68 ± 12 |

TABLE 7

Clinical mastitis cases in cows challenged with S.aureus strain 32V. Data are numbers of cows clinical per number challenged.

| Time post-challenge (days) | Vaccinates | Controls |
|---|---|---|
| 0 | 0/9 | 0/8 |
| 1 | 1/9 | 4/8 |
| 2 | 1/9 | 3/8 |
| 3 | 0/9 | 2/8 |
| 4 | 3/9 | 3/8 |
| 7 | 3/9 | 6/8 |
| 11 | 2/9 | 5/8 |
| 14 | 4/9 | 6/8 |
| 18 | 3/9 | 6/8 |
| 21 | 4/9 | 5/8 |
| 25 | 2/9 | 5/8 |

REFERENCES

1. Beining, P. R. and Kennedy, E. R. (1963), *J.Bact.* 85:732.
2. Bracewell, C. D., and Pattison, I. H. (1958), *J.comp.Path.* 68:121.
3. Bridre, J. (1907), *Bull. Soc. Cent. Med.Vet.* 61:500.
4. Butt, E. M., Bonynge, C. W. and Joyce, R. L. (1936), *J.Inf.Diseases.* 58:5–9.
5. Caputy, G. G. and Casterton, J. W. (1982), *Infect.Immun.* 36:759.

6. Colditz, I. G. and Watson, D. L. (1982a), *Res.Vet.Sci.* 33:146.
7. Colditz, I. G. and Watson, D. L. (1982b), *Microbiol. Immunol.* 26:1171.
8. Derbyshire, J. B. (1960b), *J.comp.Path* 70:222.
9. Derbyshire, J. B. (1961a), *J.comp.Path.* 71:146.
10. Derbyshire, J. B. (1961b), *Res.vet.Sci.* 2:112.
11. Kennedy, J. W., Watson, D. L. and Bennell, M. A. (1981), *Vet.Immunol. Immunopathol.* 2:367.
12. Kennedy, J. W. and Watson, D. L. (1982), *Aust.J.exp.Biol.Med.Sci* 60:643.
13. Lascelles, A. K. and McDowell, G. H. (1984), *Transplant Rev.* 19:170.
14. Minett, F. C. (1939), *J.comp.Path.* 52:167.
15. Norcross, N.L. and Opdebeeck, J.P. (1983), *Vet.Microbiol.* 8:397.
16. Singleton, L., Ross, G. W., Stedman, R. A. and Chanter, K. V. (1967), *J.comp.Path.* 77:279.
17. Watson, D. L. (1975), *Res.vet.Sci.* 19:288.
18. Watson, D. L (1976), *Immunology* 31:159.
19. Watson, D. L. (1982), *Res.vet.Sci* 32:311.
20. Watson, D. L. (1984), *J.Dairy Sci* 67:2608.
21. Watson, D. L. and Lees, C. G. (1978), *Aust.vet.J.* 54:374.
22. Watson, D. L. and Prideau, J. A. (1979), *Microbiol. Immunol.* 23:543.
23. Watson, D. L. and Kennedy, J. W. (1981), *Aust.vet.J.* 57:309.
24. Yokomizo, Y. and Isayama, Y. (1978), *Microbiol. Immunol.* 2:1.

I claim:

1. A killed vaccine effective in the immunization of ruminants against intramammary challenge by *S. aureus* and other species of the genes Staphylococcus, which comprises the antiphagocytic in vivo antigen(s) produced by the in vitro culture of a pseudocapsule—producing strain of *S. aureus* in a nutrient growth medium which is enhanced by the addition of milk or a milk component thereto.

2. A killed vaccine effective in the immunization of ruminants against intramammary challenge by *S. aureus* and other species of the genes Staphylococcus, which comprises the antiphagocytic in vivo antigen(s) produced by the in vitro culture of *S. aureus* strain J.G.80 in a nutrient growth medium which is enhanced by the addition of milk or a milk component thereto.

3. A vaccine according to claim 2, further comprising an adjuvant which promotes the production of $IgG_2$ subtype antibodies.

4. A vaccine according to claim 3, wherein said adjuvant is dextran sulphate.

5. A vaccine according to claim 2, further comprising a toxoid component comprising toxoided beta-hemolysin secreted as an exotoxin by *S. aureus*.

6. A method of immunizing a ruminant against *Staphylococcal mastitis* which comprises administering to the ruminant an effective amount of a vaccine according to claim 2.

7. A method according to claim 6, wherein said vaccine further comprises a toxoid component comprising toxoided beta-hemolysin secreted as an exotoxin by *S. aureus*.

8. A method according to claim 6, wherein there is administered separately to said ruminant a toxoid component comprising toxoided beta-hemolysin secreted as an exotoxin by *S. aureus*.

9. A vaccine according to claim 1, further comprising an adjuvant which promotes the production of $IgG_2$ subtype antibodies.

10. A vaccine according to claim 3, wherein said adjuvant is dextran sulphate.

11. A vaccine according to claim 1, further comprising a toxoid component comprising toxoided beta-hemolysin secreted as an exotoxin by *S. aureus*.

12. A method of immunising a ruminant against staphylococcal mastitis, which comprises administering to the ruminant an effective amount of a vaccine according to claim 1.

13. A method according to claim 12, wherein said vaccine further comprises a toxoid component comprising toxoided beta-hemolysin secreted as an exotoxin by *S. aureus*.

14. A method according to claim 12, wherein there is administered separately to said ruminant a toxoid component comprising toxoided beta-hemolysin secreted as an exotoxin by *S. aureus*.

* * * * *